United States Patent [19]

Pasricha et al.

[11] Patent Number: 5,437,291
[45] Date of Patent: Aug. 1, 1995

[54] METHOD FOR TREATING GASTROINTESTINAL MUSCLE DISORDERS AND OTHER SMOOTH MUSCLE DYSFUNCTION

[76] Inventors: Pankai J. Pasricha, 5007 Southern Star Ter., Columbia, Md. 21044; Anthony N. Kalloo, 10708 Forestgate Pl., Glenndale, Md. 20769

[21] Appl. No.: 112,088

[22] Filed: Aug. 26, 1993

[51] Int. Cl.$^6$ ............................................. A61B 19/00
[52] U.S. Cl. ..................................... 128/898; 604/19; 604/49; 604/51; 514/210; 424/236.1; 424/239.1; 424/581
[58] Field of Search ....................... 128/898, DIG. 25; 604/19, 49; 514/906; 424/78.01

[56] References Cited

U.S. PATENT DOCUMENTS

| | | | |
|---|---|---|---|
| 4,203,983 | 5/1980 | Yelnosky et al. | 424/249 |
| 4,713,391 | 12/1987 | Chiang et al. | 514/412 |
| 4,725,593 | 2/1988 | Davis | 514/210 |
| 4,904,673 | 2/1990 | Eberlein et al. | 514/330 |
| 4,927,629 | 5/1990 | Bing . | |
| 4,932,936 | 6/1990 | Dykstra et al. . | |
| 4,957,941 | 9/1990 | Davis et al. . | |
| 5,053,005 | 10/1991 | Borodic . | |
| 5,071,844 | 12/1991 | Alker et al. . | |
| 5,145,859 | 9/1992 | Fleischmann | 514/356 |
| 5,171,217 | 12/1992 | March et al. . | |
| 5,298,019 | 3/1994 | Borodic | 128/898 |

FOREIGN PATENT DOCUMENTS

WO93/05800 4/1993 WIPO .

OTHER PUBLICATIONS

Carpenter "Potentiation of Nerve-Induced Bladder Responses by Tetraethylammonium in Relation to Junctional and Extrajunctional Muscarinic Receptors," *Br. J. Pharmac.*, 64:331–339 (1978).
Dykstra, et al., "Effects of Botulinum a Toxin on Detrusor-Sphincter Dyssynergia in Spinal Cord Injury Patients," *J. Urology*, 139:919–922 (May 1988).
Dykstra, et al., "Treatment of Detrusor-Sphincter Dyssynergia With Botulinum A toxin: A Double-Blind Study," *Arch Phys Med Rehabil*, 71:24–26 (Jan. 1990).
Carpenter, "Motor Responses of the Urinary Bladder and Skeletal Muscle in *Botulinum* Intoxicated Rats," *J. Physiol.* 188:1–11 (1967).
Pasricha, et al., "Treatment of Achalasia With Intrasphincteric Injection of Botulinum Toxin-Results of a Pilot Study," *AGA/AASLD Abstracts*, May 1993.
Pasricha, et al., "Treatment of Sphincter of ODDI(SO) Dysfunction With Botulinum Toxin (BoTx) Injection--Case Report," *ASGE Abstract*, May 1993.
Pasricha, et al., "Injection of Botulinum Toxin (BoTx) Into The Distal Esophageal Sphincter (DES) in Piglets-A Unique Investigative Technique with Potential Therapeutic Uses," *Amer. J. Gastroenterology*, 87:1255, abstract (1992).
Pasricha, et al., "Botulinum Toxin for Achaiasia," *The Lancet*, 341:244–245 (1993).
Bigalke, et al., "Blackade by Tetanus and Botulinum A Toxin of Postganglionic Cholinergic Nerve Endings in the Myenteric Plexus," *Naunyn-Schniedebergs's Arch. Pharmacol.*, 312:255–253 (1980).

(List continued on next page.)

*Primary Examiner*—John D. Yasko
*Assistant Examiner*—Chalin Smith

[57] ABSTRACT

Direct injection of sphincteric botulinum toxin is disclosed as an effective, safe and simple method of treatment for disorders of gastrointestinal muscle or smooth muscles elsewhere in the body, with results that appear to be sustained for several months. Muscle disorders which are suitable for such treatment include achalasia, isolated disorders of the lower esophageal sphincter, gastroparesis, hypertrophic pyloric stenosis, sphincter of Oddi dysfunction, short-segment Hirschsprung's, anal fissure, hemorrhoids, proctalgia fugax, irritable bowel syndrome, disorders of the upper esophageal sphincter, vasospastic disorders, and disorders of uterine and bladder spasm. Devices suitable for delivering this therapy are also disclosed.

24 Claims, 13 Drawing Sheets

OTHER PUBLICATIONS

Jankovic, et al., "Therapeutic Uses of Botulinum Toxin," *The New Engl. J. Med.*, 324:1186–1194 (1991).

Lees, "Botulinum Toxin," *BMJ*:305(6863):1169–1170 (1992).

Dickson, et al., "Botulism: Studies on the Manner in Which the toxin of Clostridium Botulinum Acts Upon the Body," *J. Exper. Med.*, 37:711–731 (1923).

MacKenzie, et al, "The Effects of Purified Botulinum Neurotoxin Type A on Cholinergic, Adrenergic, and Non-Adrenergic, Atropine-Resistant Neuromuscular Transmission," *Neuroscience*, 7(4):997–1006 (1982).

International Search Report for PCT/US 94/09759 Dated Dec. 21, 1994.

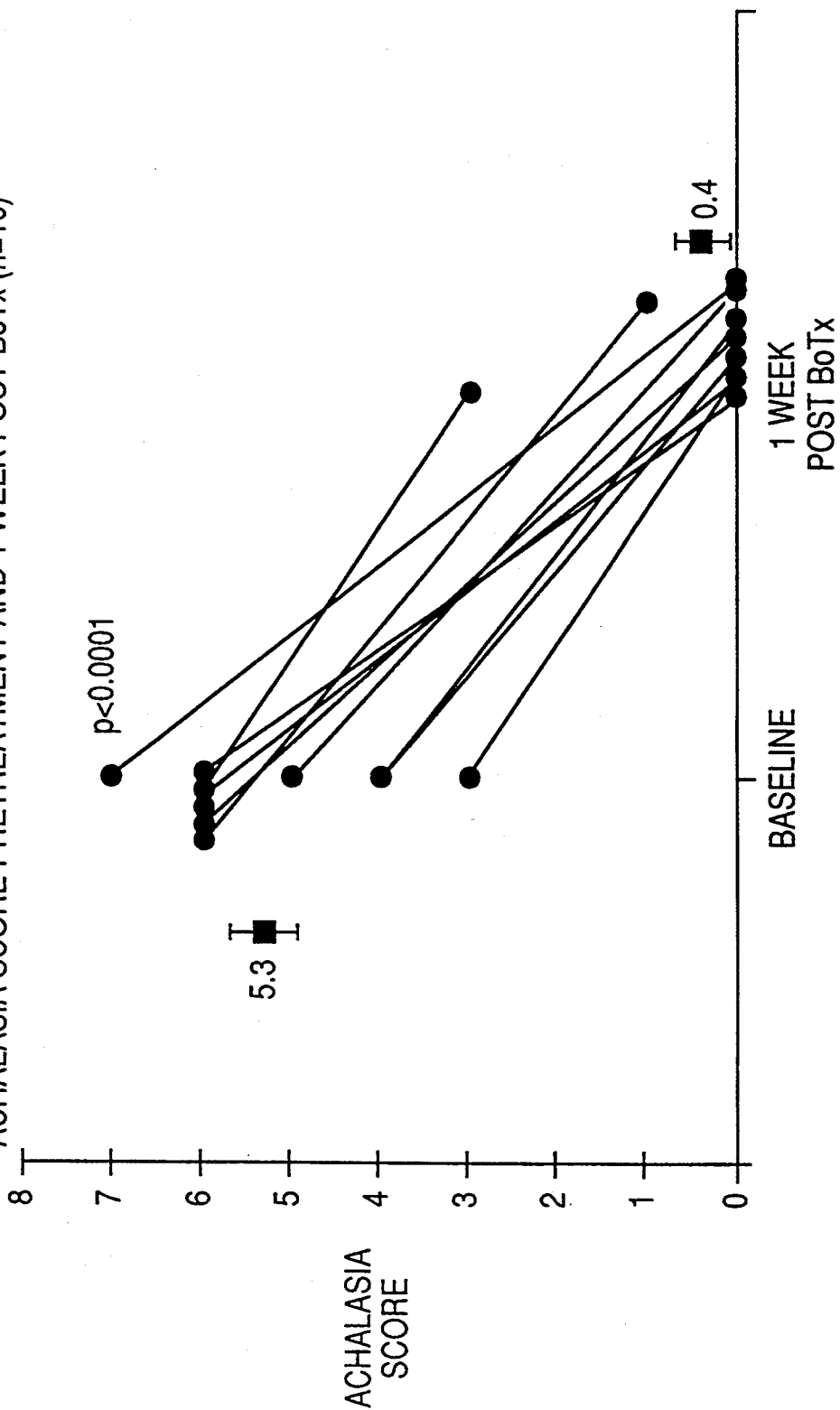

FLUID FOR RECONSTITUTION

METHOD FOR TREATING GASTROINTESTINAL MUSCLE DISORDERS AND OTHER SMOOTH MUSCLE DYSFUNCTION

TECHNICAL FIELD OF THE INVENTION

The invention relates to the field of smooth muscle disorders. In particular, the invention relates to treatment of gastrointestinal disorders, vasospastic disorders, uterine cramping, and other disorders of smooth muscle.

BACKGROUND OF THE INVENTION

Botulinum toxin (BoTx) has long been known as one of the most potent inhibitors of neuromuscular transmission (by blocking the release of acetylcholine from nerve endings) and has been used to treat several conditions where spasm of skeletal muscle is felt be an important contributory factor. However, until now there had been no attempt to explore the use of this unique biological agent in the treatment of disorders of gastrointestinal muscle or other disorders of smooth muscle.

The muscle in the gastrointestinal tract differs from muscle elsewhere in two major ways. First, most of the muscle in the gastrointestinal tract is of a type called smooth muscle. There are several fundamental differences between the way smooth muscle and skeletal muscle function. First, smooth muscle lacks a discrete end-plate (a defined region of interaction between the nerve ending and muscle, as seen in skeletal muscle); instead nerve fibers run from each axon parallel to the muscle bundle and end somewhat arbitrarily at various points along its length. Secondly, unlike skeletal muscle, smooth muscle cells are coupled electrically within large bundles by means of connecting bridges. An electrical event at any region in the bundle is therefore conducted in a decremental fashion to other regions. Thirdly, each muscle bundle receives input from multiple axons in the form of either excitatory or inhibitory signals (see below). This is in contrast to skeletal muscle outside the gastrointestinal tract, where typically only one type of neurotransmitter is operative.

In addition, the gastrointestinal muscle is organized and regulated very differently than muscle elsewhere. Both skeletal and smooth muscle in the gastrointestinal tract are under the control of the enteric nervous system which is an extremely complex network of nerves and muscles, that resides within the gastrointestinal wall and orchestrates the entire digestive process including motility, secretion and absorption. The enteric nerves are also organized into interconnected networks called plexuses. Of these, the myenteric plexus, situated between the circular and longitudinal muscle layers, is the main modulator of gastrointestinal motility. It receives input from both the central nervous system (via vagal and sympathetic pathways) as well as from local reflex pathways. Its output consists of both inhibitory and excitatory signals to the adjacent muscle.

The final neural pathway regulating muscle activity in the gastrointestinal tract is therefore represented by the neurons of the myenteric plexus. A useful, if somewhat simplistic concept is to visualize net muscle tone in the gastrointestinal tract as that resulting from the balance between the opposing effects of two neuronal systems in the myenteric plexus: one causing the muscle to contract (mainly via acetylcholine) and the other causing it to relax. Both types of neurons, however, are activated by acetylcholine within the myenteric plexus.

The role of acetylcholine in the regulation of gastrointestinal muscle tone is therefore complex. Acetylcholine directly released by effector nerves near the muscle causes contraction; however, within the royenteric plexus, it may result in inhibition or excitation. This is in contrast to skeletal muscle outside the gastrointestinal tract which is directly innervated by nerves emanating from the central nervous system. The interaction between nerve and muscle in skeletal muscle outside the gastrointestinal tract is far more simple: nerves release acetylcholine which causes the muscle to contract.

Finally, the myenteric plexus is probably the most important but not the only determinant of muscle tone in the gastrointestinal tract. In fact, basal smooth muscle tone may be visualized as resulting from the sum of many different factors including intrinsic (myogenic) tone, and circulating hormones, in addition to nerve activity.

It should be clear therefore, that the regulation of gastrointestinal tract muscle motility is far more complex than that of skeletal muscle outside the gastrointestinal tract. While there have been isolated reports on the effects of botulinum toxin on in vitro preparations of gastrointestinal smooth muscle, the regulation of gastrointestinal muscle is so complex that the physiological consequences of blocking neurotransmitter release (by using toxin such as botulinum) in humans or in live animals were not predictable prior to the present invention.

There is a need in the medical arts for methods and devices for treatment of gastrointestinal disorders including achalasia, other disorders of the lower esophageal sphincter, sphincter of Oddi dysfunction, irritable bowel syndrome, etc., which treatments will be long-lasting and devoid of significant rates of complication.

SUMMARY OF THE INVENTION

It is an object of the invention to provide methods for in vivo treatment of mammals with dysfunctional gastrointestinal muscle or disorders of smooth muscles elsewhere in the body.

It is another object of invention to provide a device for in vivo treatment of mammals with dysfunctional gastrointestinal muscle or smooth muscles elsewhere in the body.

These and other objects are provided by one or more of the embodiments described below. In one embodiment of the invention a method for in vivo treatment of smooth muscle disorders of a mammal, comprises injecting directly into a smooth muscle in a mammal an amount of a neurotoxin which inhibits neurotransmitter release from nerve terminals.

In another embodiment of the invention a method is provided for in vivo treatment of disorders of a gastrointestinal muscle in the enteric nervous system of a mammal. The method comprises injecting directly into the enteric nervous system in a mammal an amount of a neurotoxin which inhibits neurotransmitter release from nerve terminals.

In another embodiment of the invention a device is provided for injecting a neurotoxin into a gastrointestinal muscle in the body. The device comprises a hollow needle to pierce a target tissue; a deformable capsule to hold a drug; a piston to press said capsule so that it releases said drug through said needle; wherein said needle is in direct contact with a first end of said capsule, and wherein said piston is in contact with a second end of said capsule, and wherein said first and second ends are oppositely disposed within said sheath.

In still another embodiment of the invention a device is provided for injecting a neurotoxin injecting a drug via an endoscope. The device comprises a piercing means to pierce the target tissue; a holding means to hold a drug; a pressing means to press said holding means so that it releases the drug through said piercing means; wherein said piercing means is in direct contact with the interior of a first end of said holding means and said pressing means is in contact with a second end of said holding means, and wherein said first and second ends are oppositely disposed within said encompassing means.

In yet another embodiment of the invention a drug delivery cartridge is provided for use within an endoscope. The drug delivery cartridge comprises a chamber containing a drug; a hollow needle in contact with a first end of said chamber; a coupling means for securing the chamber to an injecting means, wherein the drug delivery cartridge is positioned within an endoscope for local delivery of the drug to a target tissue.

These and other embodiments of the invention provide the art with means for treating, without significant complications, a variety of disorders which involve spasm or elevated tone of gastrointestinal muscle or smooth muscles elsewhere in the body.

BRIEF DESCRIPTION OF THE DRAWINGS

FIG. 4 shows the clinical response as measured by global Achalasia Scores before and one week after treatment with intrasphincteric botulinum toxin (BoTx) injection. All ten patients showed significant improvement.

DETAILED DESCRIPTION

Figure 1:
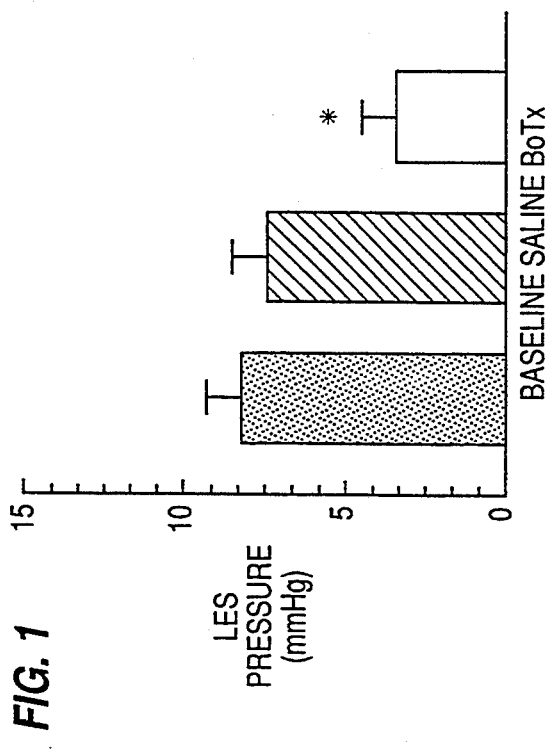
FIG. 1 shows the effect of intrasphincteric injection of BoTx on resting lower esophageal sphincter (LES) pressure in piglets.

It is a discovery of the present invention that gastrointestinal muscle or smooth muscles elsewhere in the body of a live mammal can be partially paralyzed by a neurotoxin which inhibits neurotransmitter release from nerve endings. This finding led to the discovery that local injection of such a neurotoxin into gastrointestinal muscle or smooth muscle elsewhere in the body can alleviate the symptoms of chronic smooth muscle disorders. Moreover, local injection of such a neurotoxin appears to be safe and well-tolerated in the mammals.

A number of motility disorders of the gastrointestinal tract are amenable to treatment by local injection of neurotoxin. These include upper esophageal sphincter disorder, achalasia, isolated disorders of the LES, gastroparesis, hypertrophic pyloric stenosis, sphincter of Oddi dysfunction, short-segment Hirschsprung's, irritable bowel syndrome, anal fissure, hemorrhoids, and proctalgia fugax. See Table I. In addition, other smooth muscle disorders are also amenable to local treatment with botulinum toxin. These include menstrual and pre-menstrual cramps, as well as vasospastic disorders, such as atypical angina, Berger's disease, spastic bladder, etc.

According to the method of the present invention, mammals are treated by direct (local) injection of a neurotoxin into a smooth muscle which exhibits elevated tone or spasms. Alternatively, any tissue of the enteric nervous system can be the target of the local injection. In the case where the smooth muscle is in the gastrointestinal tract, the administration is mostly conveniently accomplished using an endoscope. Typically an amount of neurotoxin is added which is effective in reducing the tone or spasms of the smooth muscle. In some cases alleviation of a symptom of the muscle disorder, such as pain, is the goal. Typically the amount of neurotoxin is between about 0.1 and 1000 units. Desirably the amount is between about 0.1 and 100 units, and most preferred is an amount between about 10 and 100 units. One International Unit (IU) of the toxin is approximately equal to the $LD_{50}$ for a 20 gram mouse.

The neurotoxin can be any which inhibits acetylcholine release from nerve endings. Such neurotoxins include botulinum toxin, tetanus toxin, and tetrodotoxin and derivatives thereof. The preferred toxin according to the present invention is botulinum toxin type A. Suitable botulinum toxin is commercially available under the trade name Oculinum from Oculinum Inc. Berkeley, Cal. The neurotoxin is supplied in lyophilized form and is reconstituted by solvation in saline. Neurotoxins can also be used which inhibit release of other neurotransmitters from nerve terminals. Such neurotransmitters include nitric oxide, GABA, serotonin, dopamine, epinephrine, and norepinephrine.

Devices particularly designed for the efficient administration of neurotoxin to smooth muscles of the gastrointestinal tract are shown in FIGS. 11-17. The devices typically comprise a holding means, such as a deformable capsule or chamber (element D shown in FIG. 11) which can be used for reconstitution of lyophilized neurotoxin. Alternatively, already reconstituted neurotoxin, or a solution of neurotoxin can also be added directly to the chamber. The chamber can have port (element C) for addition of neurotoxin or solvent.

TABLE 1

Motility disorders of the gastrointestinal tract amenable to treatment with local injection of botulinum toxin.

| Disorder | Symptoms | Proposed Target Muscle |
|---|---|---|
| Esophagus: | | |
| Upper esophageal sphincter | Dysphagia Aspiration | cricopharyngeus |
| Achalasia | Dysphagia Regurgitation | LES |
| Isolated disorders of the LES | Dysphagia Chest pain | LES |
| Stomach: | | |
| Gastroparesis | Pain, nausea | pylorus |
| Hypertonic pyloric stenosis | Vomiting | pylorus |
| Biliary: | | |
| Sphincter of Oddi Dysfunction | Abdominal Pain Pancreatitis | Sphincter of Oddi |
| Anorectal: | | |
| Anismus* | Constipation | levator ani puborectalis |
| Levator syndrome* | Pain | levator ani puborectalis |
| Short-segment Hirschsprung's | Constipation | internal anal sphincter |
| Anal fissure | Pain, discharge | internal anal sphincter |
| Hemorrhoids | Pain, bleeding discharge | internal anal sphincter |

TABLE 1-continued

Motility disorders of the gastrointestinal tract amenable to treatment with local injection of botulinum toxin.

| Disorder | Symptoms | Proposed Target Muscle |
|---|---|---|
| Proctolgia fugax | Pain | internal anal sphincter |

*Skeletal muscle

At one end of the neurotoxin holding means is a piercing means (element E) with which the gastrointestinal muscle or other smooth muscle is pierced to allow direct injection of the neurotoxin. Typically the piercing means comprises a hollow needle, such as a sclerotherapy needle. Typically the needle is about 6 mm in length and a 25 gauge needle.

Figure 12:
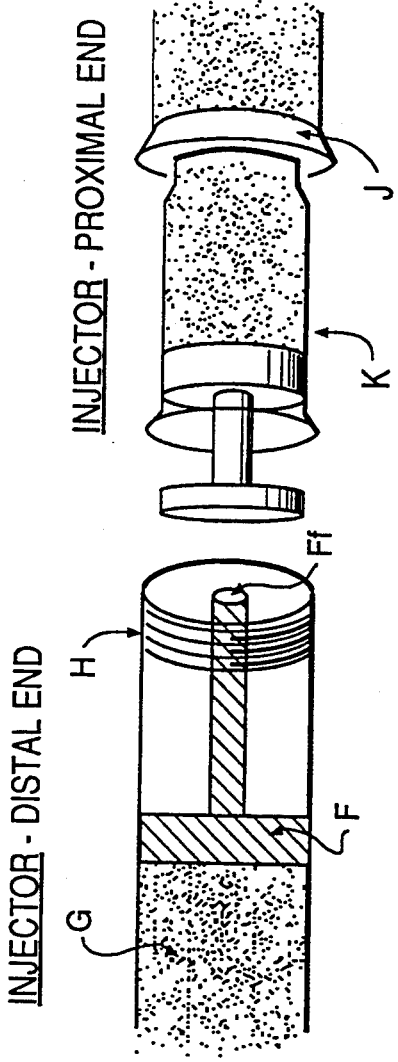
FIG. 12 shows a second portion of a device for administration of BoTx consisting of an injector. A fluid column (G) in a catheter (H) moves a plunger/rod (F/Ff) which when connected to the portion shown in FIG. 11, causes the release of BoTx from the chamber (D).

At the opposite end of the holding means from the piercing means is a pressing means (element H, FIG. 12). The pressing means can be any which is capable of deforming the holding means such that it releases the neurotoxin through the needle. Typically the pressing means can be a simple plunger piston, a screw-type piston, or a piston with an hydraulic fluid. The piston causes the chamber to contract and release its contents.

Prior art devices do not contain a holding means immediately adjacent to the needle, but instead, utilize an external reservoir of drug which is pumped through a long tube, typically on the order of 200 cm to the target site. The advantage of the disclosed device over those of the prior art is that it eliminates the "dead space" of the tube, running from outside the body to the point of injection. This provides a cost benefit, as expensive drug is not wasted in filling the tube which never reaches the target. It also provides an improvement in the accuracy of dose which can be achieved, as essentially all of the drug which is administered reaches the target muscle. As can readily be imagined, the device of the present invention will be applicable to a variety of drugs which can be administered via an endoscope. This device will find use where, as here, the drug is toxic and one wants to avoid exposure of non-target tissues and organs to the drug. Such drugs include chemotherapeutic agents.

Also provided by the present invention are drug delivery cartridges, which can be disposable units which can be combined with other non-disposable elements of a delivery system for cost effective administration. The drug delivery cartridges comprise a chamber for holding drug. Typically this will be a dried or lyophilized drug which can be reconstituted immediately before administration. Preferably the drug will be botulinum toxin A. At one end of the chamber is a needle, which is in direct or "fluid" contact with the interior of the chamber, such that upon increased pressure, drug is released through the needle into a target tissue or organ. The cartridge also comprises a coupling means (B in FIG. 11) which secures the chamber to the catheter within which the drug delivery cartridge is positioned in the body. Typically the chamber will be a deformable substance, such as plastic or rubber. Alternatively, one side of the chamber is movable so that the effective size of the chamber can be reduced to release its contents through the needle. The catheter is placed within the body within an endoscope.

DESCRIPTION OF PREFERRED EMBODIMENT

Figure 11:
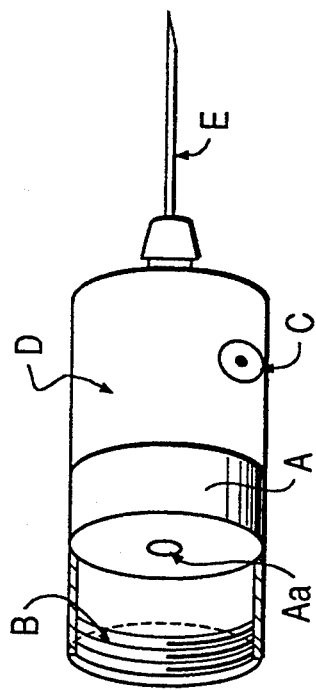
FIG. 11 shows a portion of a device (a cylinder/needle unit) for administration of BoTx, consisting of a needle (E), a chamber (D) with a threaded portion (B), and a port (C) so that BoTx can be added and/or reconstituted, and a plunger (A).

The device consists of two separate parts (a cylinder-needle unit and an injector) that can be attached to each other by means of a screw and thread mechanism. The first part, shown in FIG. 11 is a hollow plastic cylinder that consists of the following components:
- a needle (E) at one end of the cylinder that will pierce the target organ (typical dimensions: 25 gauge, 6 mm)
- a chamber (D) that contains the drug in a powder form (typical dimensions; 2.3 mm width, 1 ml total volume)
- a rubber or plastic port (C) for injection of aline or other fluid required to reconstitute the drug
- a movable plunger (A) that contains a shallow socket in its center (Aa) to accommodate the plunger rod of the injector
- a threaded portion (B) that will screw over the corresponding end of the injector The second part of the device consists of the injector, shown in FIG. 12. The distal end of the injector consists of a hollow fluid-filled (typically water) catheter. The fluid column (G) in the catheter ends in a movable plunger-rod (F and Ff). The last part of the catheter is threaded so that the corresponding part of the cylinder-needle unit can be screwed onto it. The proximal end of the injector consists of a hub (J) for attachment of a regular plastic "outer" syringe (K) that is used to push fluid within the catheter.

Typical dimensions of the injector unit (excluding the outer syringe) are: 2 mm width and 200 cm length.

Figure 13:
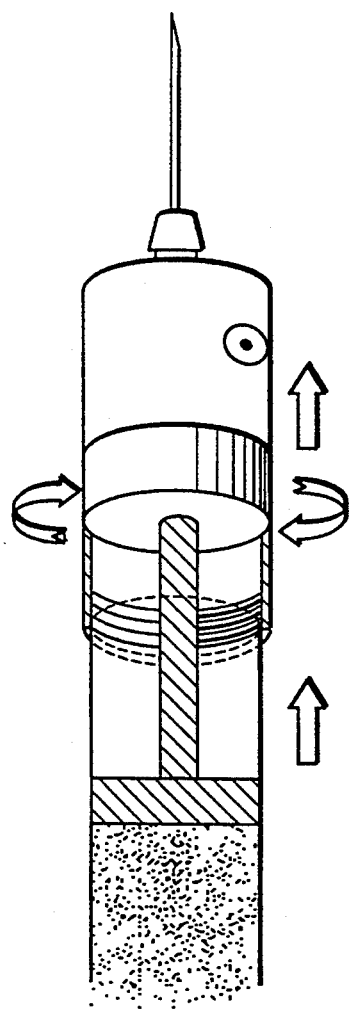
FIG. 13 shows the assembly of a device for administration of BoTx in which the cylinder/needle unit is screwed into the injector.

To assemble the device, the cylinder-needle unit is screwed onto the distal end of the injector unit until some resistance is felt, implying a snug fit between the distal end of the plunger-rod (Ff) and the socket (Aa) within the plunger of the cylinder-needle unit (A) (FIG. 13).

Figure 14:
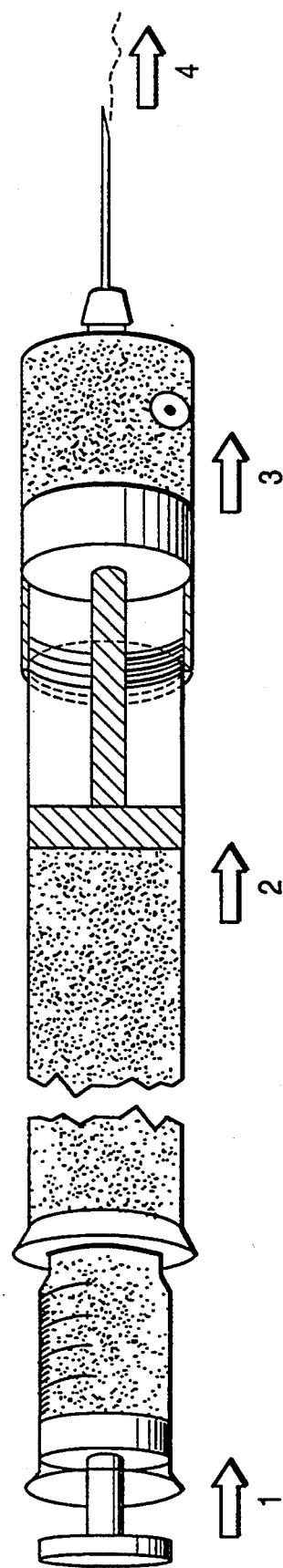
FIG. 14 shows operation of a device for administration of BoTx in which a screw-type piston is used to compress a chamber containing the neurotoxin and release the neurotoxin into the target tissue.

To operate the device, an appropriate amount of fluid is injected via the port C, to reconstitute the drug to the desired volume. The device is then passed through the biopsy channel of an endoscope. The outer syringe (K) is then attached to hub of the injector at the proximal end, which lies outside the endoscope and outside the body. The endoscope is then inserted into the body and carried to the target organ by standard means. On reaching the desired target, the distal end of the device is pushed out of the scope, and the needle is inserted at the point and depth desired. As shown in FIG. 14, the desired amount of drug is injected by pushing the plunger of the outer syringe (1). The plunger in turn pushes the fluid in the catheter against the plunger-rod (2) that then pushes the plunger within the cylinder—needle unit (3), causing drug to be delivered via the needle (4). After completion of the injection, the device is withdrawn into the biopsy channel of the endoscope, so that the organs are no longer exposed to the needle.

Figure 15:
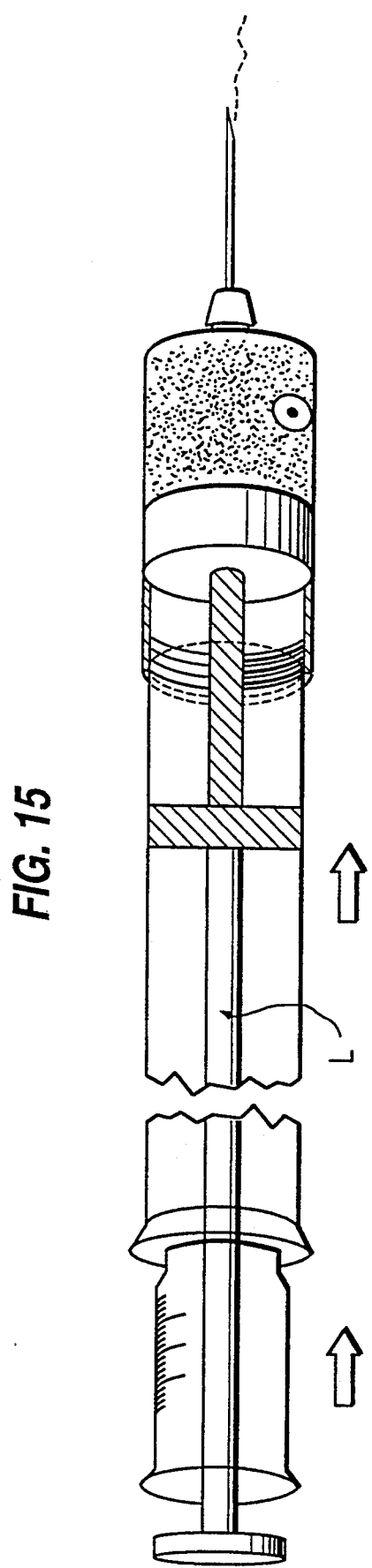
FIG. 15 shows an alternate injector system in which a cable (L) replaces the fluid filled column (G) shown in FIG. 12.

An alternative design replaces the fluid-filled column in the catheter with a long cable (L) that is attached to the plunger-rod. To operate the device, the proximal end of the cable is then mechanically pushed distally, resulting in movement of the plunger-rod against the plunger (FIG. 15).

Figure 16:
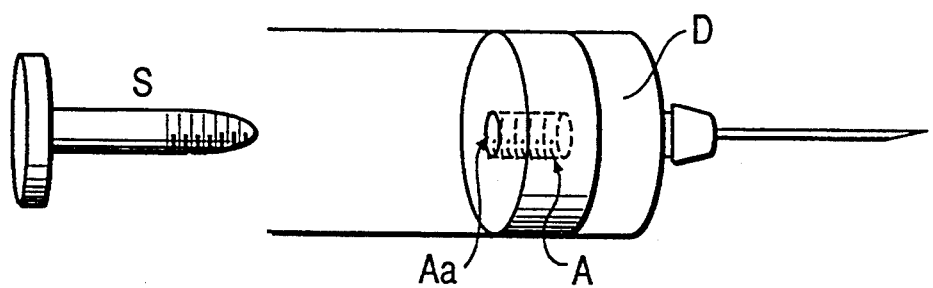
FIG. 16 shows assembly of an alternate means for reconstituting drug in which a small shaft with a handle (S) is withdrawn from the chamber (D) causing negative pressure in the chamber.
Figure 17:
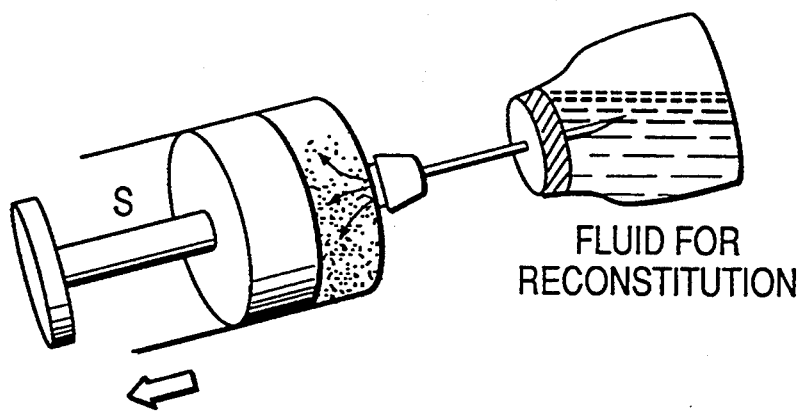
FIG. 17 shows the operation of the filling means of FIG. 16 to reconstitute the BoTx in solution.

An alternative way to reconstitute the drug is shown in FIG. 16. The socket (Aa) in the plunger A of the cylinder-needle unit is threaded so as to be a female port, into which Is screwed a small shaft with a handle (S). To draw the fluid into the cylinder, the shaft is screwed into the plunger. The needle is then inserted into a vial containing the desired fluid for reconstitution and the plunger is pulled back by the shaft, drawing fluid into the cylinder (FIG. 17). Once the desired amount is withdrawn, the shaft is then unscrewed, and the cylinder-needle unit is assembled onto the injector unit as illustrated before.

EXAMPLES

Example 1

This example demonstrates that toxin of *Clostridium botulinum* (BoTx) is a potent inhibitor of resting LES tone.

Measurements of baseline LES pressure by the station pull-through method were obtained in five piglets. Thereafter, normal saline was injected into the LES of all the animals, as described above. One week later, LES pressure was again measured, and BoTx (1 mL of a 10 U/mL solution in each of four quadrants for a total of 40 U) was injected into the LES. After another week, the LES pressure was again measured.

Animals and Preparation

Male piglets (Sus-scrofus domesticus), ranging in weight between 20 and 30 kg, were evaluated. After an overnight fast but access to water, presedation in the form of intramuscular ketamine (400–500 rag) was administered. Thereafter, intravenous (IV) access was established (usually in the ear lobes), and IV pentobarbital was administered (in an initial bolus of 130–195 rag) and a cuffed endotracheal tube placed. Further doses of IV pentobarbital were then administered to ensure deep anesthesia and respiration provided via mechanical ventilation, during which time the animals underwent continuous monitoring of end-expiratory $PCO_2$.

The study was approved by the Animal Care and Use Committee of Johns Hopkins University.

Esophageal Manometry

LES pressures were measured by one of two methods: (1) the station pull-through method, using a three-lumen water-filled polyvinyl tube assembly (OD 4 mm), which was used to determine the effect of BoTx on resting LES pressure; or (2) the use of an esophageal catheter equipped with a DENTSLEEVE (Arndorfer Medical Specialties, Greendale, Wis.), which was used to monitor real-time changes in LES pressure in response to IV administered drugs or hormones. The DENTSLEEVE method routinely yielded higher values for baseline LES pressures; therefore, only one type of catheter was used for each set of experiments. The catheters were perfused with distilled water at a constant rate of 0.5 mL/min by a low-compliance pneumohydraulic system. Pressures within the catheter were transmitted to external transducers and recorded by a four-channel polygraph (Dynograph Recorder R611; Beckman Instruments, Palo Alto, Cal.). LES pressure was recorded in millimeters of mercury above mean gastric fundal pressure and measured with the ventilator shut off momentarily. The position of the LES with respect to the length of the manometric catheter was noted.

Endoscopy and Intrasphincteric Injection

Next, endoscopy was performed with a standard adult forward-viewing instrument. The site of the LES was estimated both endoscopically as well as by the previously performed manometry. At this site, normal saline or BoTx type A (Oculinum; Oculinum Inc., Cal.) was injected via a 4-mm sclerotherapy needle passed thorough the biopsy channel of the endoscope and inserted into the esophageal wall. One milliliter of a 10 U/mL solution was injected into each of four quadrants, for a total of 40 U.

FIG. 1 shows the effects of intrasphincteric injection of normal saline (as control) and BoTx on resting LES pressure in five piglets, measured by the station pull-through method. Mean baseline LES pressure at the start of the experiment was 8.2±1.5 mm Hg. One week after injection of normal saline, mean LES pressure was 7.3±2.1 mm Hg, not significantly different from baseline ($P>0.45$). After intrasphincteric injection of BoTx, however, mean LES pressure was 3.2±1.0 mm Hg, a reduction of about 60% from baseline ($P<0.01$). The response of the LES to the IV administration of edrophonium (Tensilon; ICN Pharmaceuticals Inc., Costa Mesa, Cal.) and cholecystokinin octapeptide (CCK-8) (Kinevac; ER Squibb & Sons, Princeton, N.J.) in three additional piglets was also measured. LES pressures, measured by a DENTSLEEVE, were recorded in response to IV edrophonium (5 rag). After a washout period of 10 minutes, CCK (5 μg IV) was then administered. Subsequently, BoTx was injected into the LES, as described above, and the experiment was repeated 1 week later.

Figure 2A:
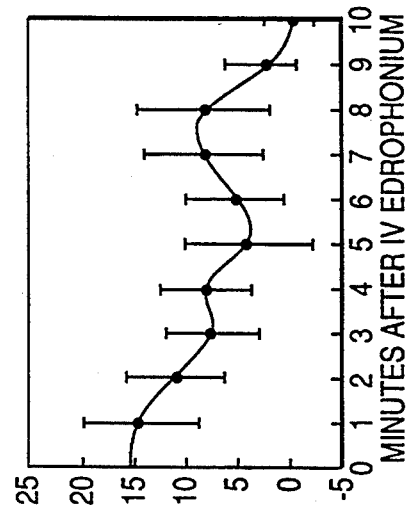
FIG. 2A and 2B show the effect of intrasphincteric injection of BoTx on LES response to edrophonium. 5 mg of edrophonium were administered intravenously before (FIG. 2A) and 1 week after (FIG. 2B) intrasphincteric injection of BoTx.
Figure 2B:
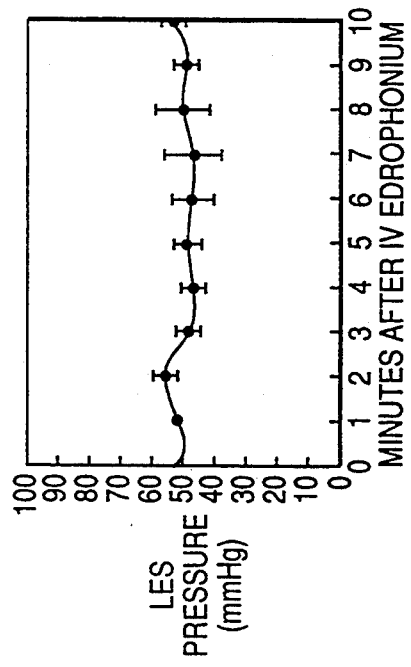

FIG. 2 shows that edrophonium did not cause any significant change in LES pressure in untreated piglets. However, after intrasphincteric BoTx injection, there was a marked reduction in LES pressure in response to edrophonium injection.

Figure 3A:
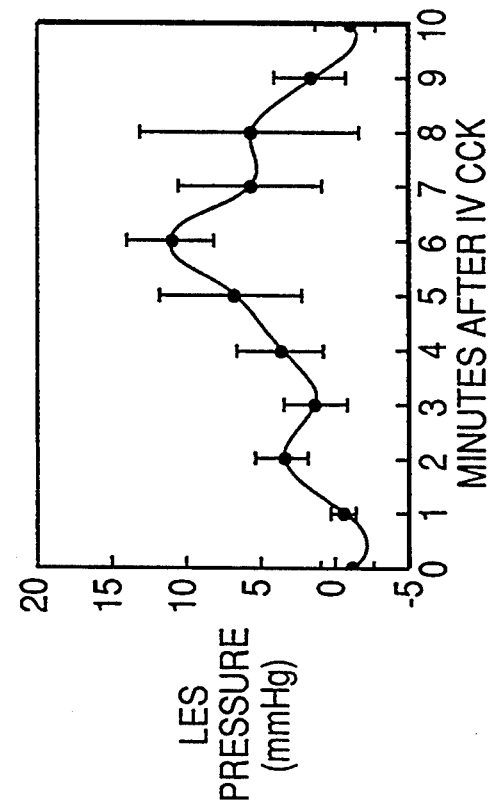
FIGS. 3A and B show the effect of intrasphincteric injection of BoTx on LES response to cholecystokinin octapeptide (CCK).
Figure 3B:
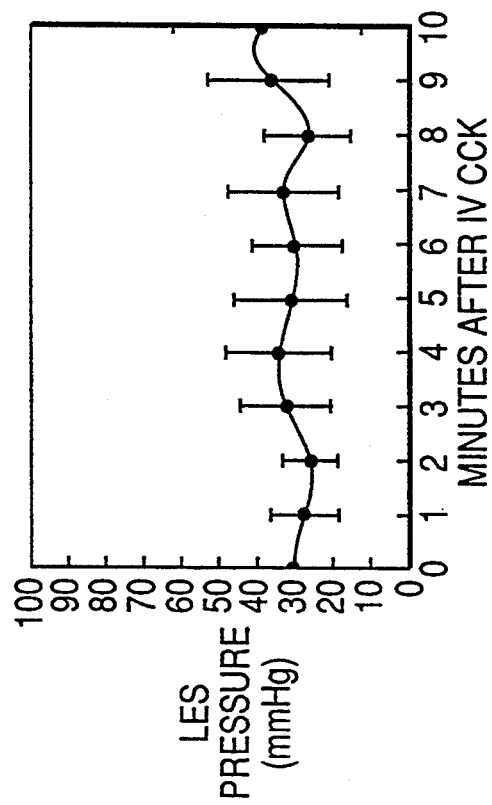

Intrasphincteric BoTx also altered the response of the LES to CCK (FIG. 3). In untreated piglets, CCK did not cause any significant change in LES pressure. However, after intrasphincteric BoTx injection, a significant increase in LES pressure was seen in response to CCK. It should be noted that despite what was felt to be an adequate washout period (10 minutes) in between injections, basal LES pressure did not return to the levels seen before edrophonium injection in both the pre- and post-BoTx piglets.

Toxicity and Pathological Changes in the LES

No evidence of adverse effects to BoTx injection were apparent. Pigs appeared healthy, had a hearty appetite, and continued to gain weight. Follow-up endoscopy 1 week after injection did not show any evidence of esophagitis or other mucosal damage. At necropsy, performed 1 week after the injection, the gastroesophageal junction appeared normal without any serosal inflammation. Histologically, the distal esophagus appeared normal under light microscopy.

Data Analysis

Data were analyzed using Student's two-tailed t test or by analysis of variance (ANOVA), as appropriate. Wherever required, means are given along with standard deviations.

Example 2

This example demonstrates the successful treatment of achalasia with a neuromuscular toxin. Achalasia is a disorder of esophageal motility characterized by absent peristalsis, an elevated lower esophageal sphincter (LES) pressure, and a failure of the LES to relax with swallowing.

All patients underwent pretreatment evaluation consisting of clinical assessment, video-esophagograms, radionuclide esophageal retention studies and esophageal manometry. After a careful diagnostic upper endoscopy, botulinum toxin was injected into the LES, as described below. Approximately one week later, the patients were reevaluated clinically, as well by the previously mentioned objective esophageal tests.

Patients

We prospectively evaluated symptomatic adult patients with clinical, radiographic and manometric features characteristic of achalasia.

Clinical Assessment

Symptomatic response was evaluated by two methods. The first consisted of a modified Achalasia Score (Eckardt VF, et al., Gastroenterology 1992;103:1732-38), which was a sum of the individual scores of three major symptoms, namely: dysphagia, regurgitation and chest pain. Each of these was graded as follows: 0:none, 1:occasional, 2:daily, 3:each meal. Thus the maximum total score achievable was 9.

The clinical response was also analyzed using the more traditional Vantrappen criteria (Vantrappen G. and Hellemans J., Gastroenterology 1980:79:144–154). This system classifies clinical response into one of 4 categories namely: excellent (asymptomatic), good (dysphagia less than 5 minutes and less than once a week, relieved by drinking fluid), moderate (dysphagia more than once a week but less than 5 minutes) or poor (dysphagia more frequent or of longer duration than the foregoing, or the presence of weight loss or regurgitation).

Patients were questioned daily for the first week and periodically thereafter for the occurrence of potential complications such as fever, chest pain, systemic weakness, flu-like illness, and reflux symptoms.

Esophageal Manometry

Esophageal manometry was obtained using a solid state motility probe (Series P33, Konigsberg Instruments Inc., Pasadena, Cal.), with two circumferential (outer diameter 5.2 ram, length 3.1 ram) and two directional sensors, connected to an on-line computer for data collection and graphic display. A slow station pull-through method was performed through both circumferential sensors. LES pressures were analyzed in a blinded fashion by a single experienced operator, using the end-expiratory pressure in the area of the highest pressure segment. Segments of the tracing showing pressure changes related to swallowing were avoided. The LES pressure was calculated by averaging the values thus obtained from each of the two circumferential catheters.

Esophageal Retention Studies

After an overnight fast, patients were asked to ingest a corn-flake meal with milk containing 0.531 mci $^{99m}$Te DTPA. Subsequently, serial dynamic images were obtained with the subject sitting erect in front of a gamma camera. Retention was expressed as the percentage of ingested radioactivity counted in the esophagus at 2, 5, 10 and 20 minutes after ingestion.

Video-Esophagography

Patients were asked to swallow a thin liquid barium sulfate suspension and a video recording was made of each swallow. The maximal diameter of the esophageal body was measured from spot films taken during the course of this study.

Endoscopy and Intrasphincteric Injection of Botulinum Toxin

After the above tests had been obtained, patients underwent a flexible upper endoscopy (using routine sedation), and a careful examination of the esophagus, stomach and duodenum was performed. Subsequently, botulinum toxin (Oculinum, Oculinum Inc., Berkeley, Cal.) was injected via a 5 mm sclerotherapy needle into the LES as estimated endoscopically. Aliquots of 1.0 ml (20 units botulinum toxin/ml) were injected into each of four quadrants, for a total of 80 units. The total time for the entire endoscopic procedure is about 10–15 minutes. Patients went home directly, as soon as they had recovered from the sedation and were allowed to eat later the same day.

Statistical Analysis

Data was analyzed using Student's t-test or Analysis of Variance (ANOVA) as appropriate. Results are expressed as means±standard error (S.E.), unless otherwise specified.

Patient Characteristics

A total of 12 patients were enrolled in the study. Two were subsequently excluded: one patient because of the presence of infiltrating adenocarcinoma at the gastroesophageal junction and the other because of a lack of a defined sphincter zone on manometry (this patient had previously undergone a Heller myotomy). Of the 10 patients finally included, 4 were male and 6 were female. The man age in this patient population was 51 years, with a range of 24 to 80 years. Patients had been symptomatic for an average of 4.7 years. All but one patient had undergone esophageal dilation (pneumostatic dilation in 7 patients and bougie dilatation in 2) at least once at some point in their history, with relief that was either unsatisfactory or transient.

Initial Clinical Response to Intrasphincteric Botulinum Toxin

The clinical response to botulinum toxin was dramatic, with all patients showing significant improvement (FIG. 4). Achalasia scores fell from a pretreatment average of 5.3±0.4 to 0.4±0.3 one week after treatment with botulinum toxin ($P<0.0001$).

Figure 5:
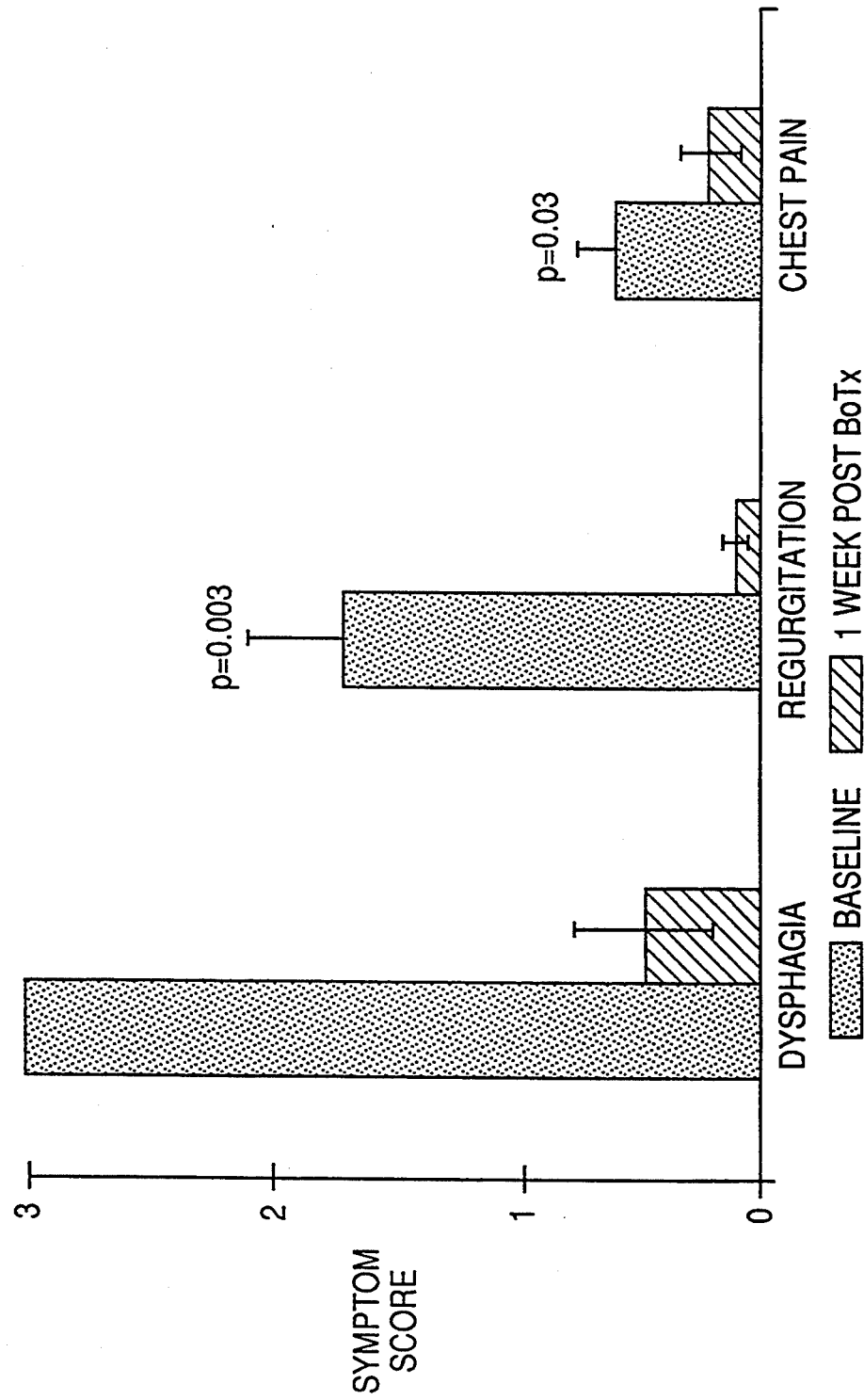
FIG. 5. shows clinical response with respect to individual symptom components of the Achalasia Score. Baseline (before treatment) scores are represented by the solid bars, while the hatched bars represent the scores one week after treatment with intrasphincteric botulinum toxin (BoTx).

On further analysis, significant and impressive improvements were seen in all three components of the score (FIG. 5). Thus, all patients had maximally severe dysphagia before treatment, resulting in a mean score of 3. This decreased to 0.5 after treatment. Similarly, regurgitation improved from a pretreatment average of 1.7, to 0.2 one week after treatment. Chest pain or discomfort, though not uniformly present in our patients, also decreased significantly following treatment.

Figure 6:
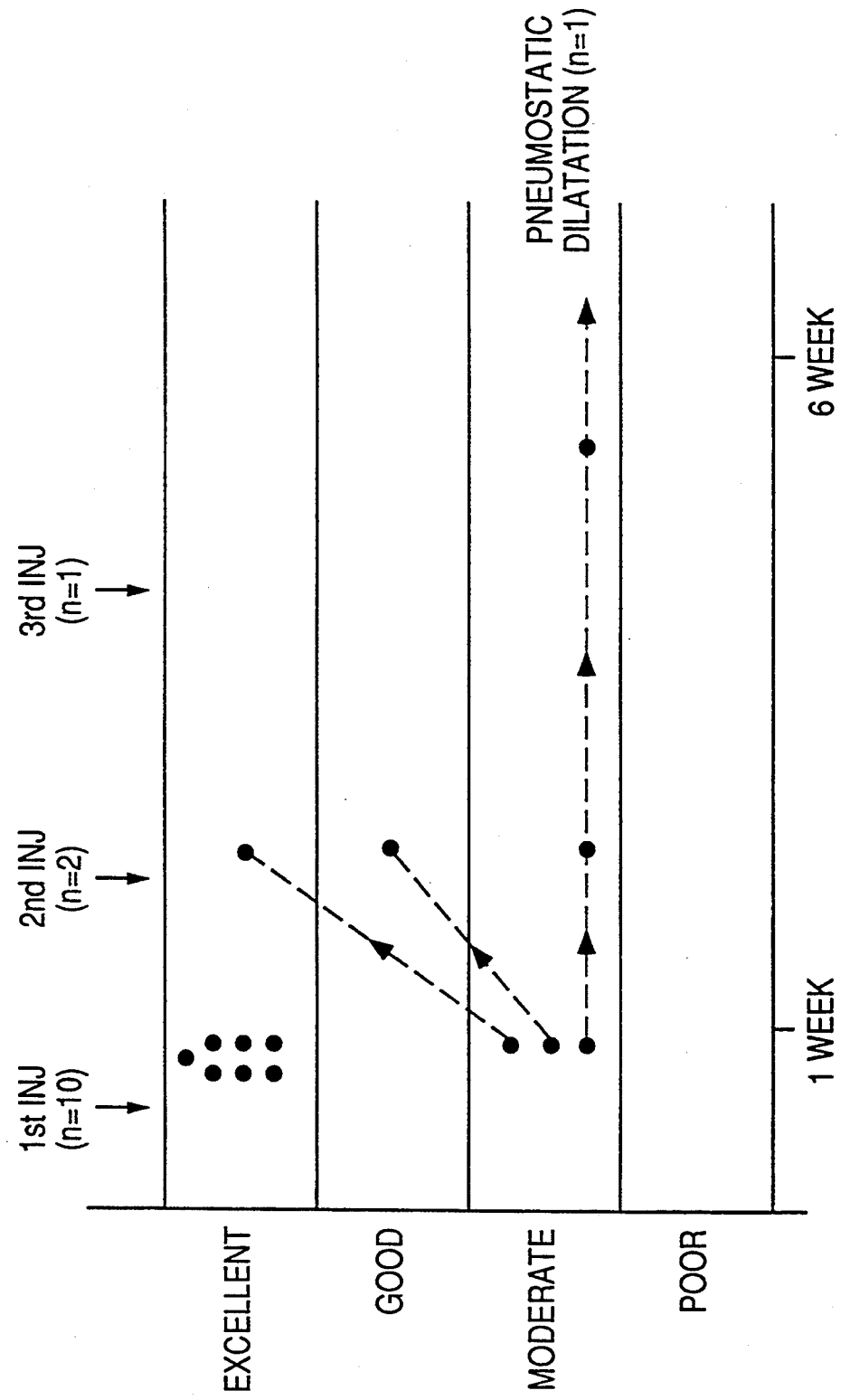
FIG. 6 shows initial clinical response as analyzed using the Vantrappen criteria. Seven out of ten patients (represented by the seven dots seen in the upper left hand corner) achieved an excellent response after one injection. The three remaining patients (denoted by the dots further below in the figure), had a moderate improvement in their symptoms after the first injection and underwent a second injection. This resulted in significant improvement in two of the three, as can be seen by the course of the arrows. The third patient continued to be moderately symptomatic despite a total of three injections and finally underwent a pneumostatic dilatation with good results.

The clinical response was also analyzed using the Vantrappen criteria. As can be seen from FIG. 6, seven out of 10 patients achieved an excellent response after one injection alone (i.e., these patients became asymptomatic). The three remaining patients had a moderate improvement in their symptoms after the first injection and underwent a second injection. This resulted in significant improvement of two of the three. The third patient continued to be moderately symptomatic despite a total of three injections and finally underwent a pneumostatic dilatation with good results.

LES Pressure Response

Figure 7:
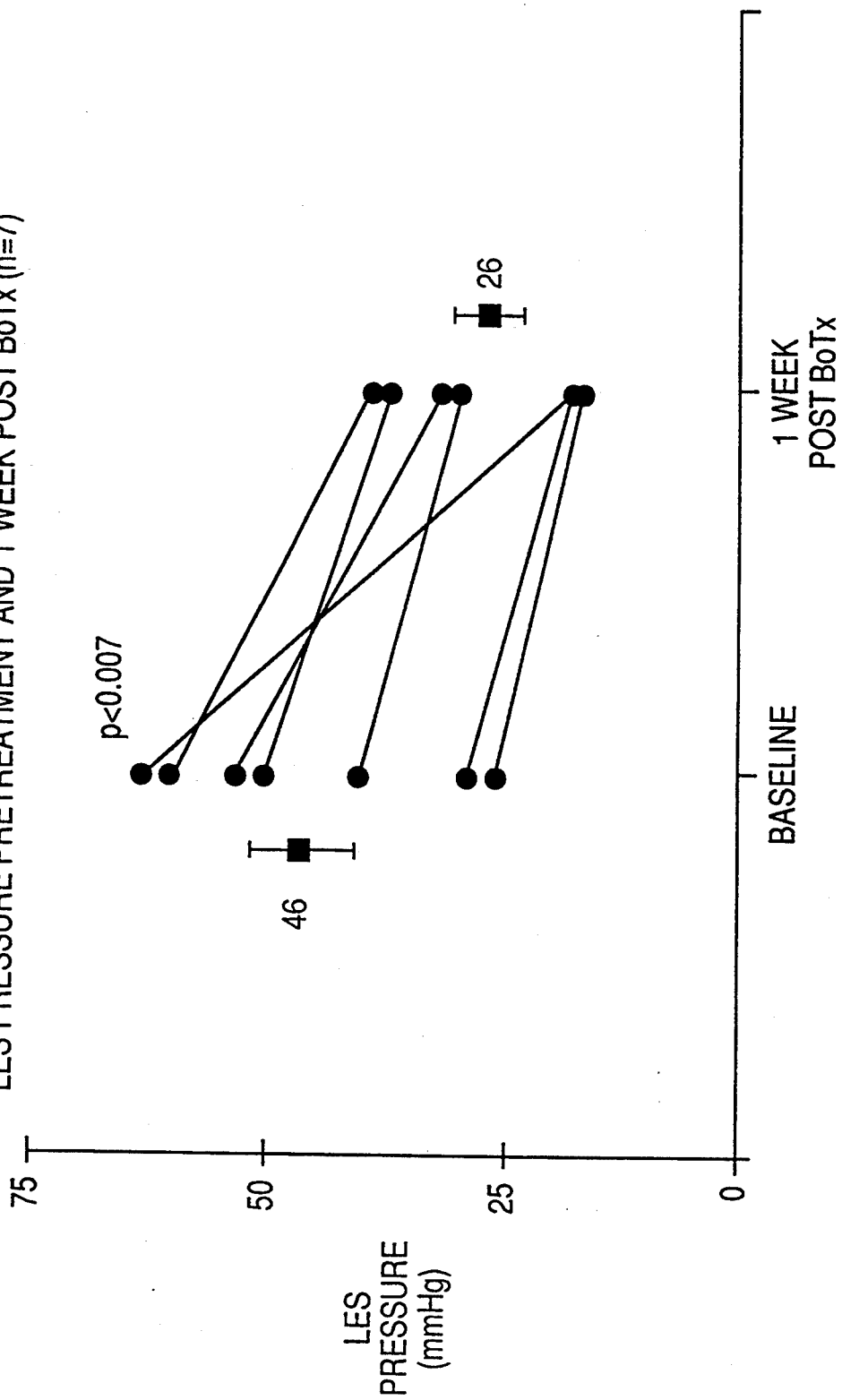
FIG. 7 shows response of lower esophageal sphincter (LES) pressures to intrasphincteric botulinum toxin (BoTx) in seven patients. The numbers on the graph represent means±S.E..

LES pressures, available for analysis in seven patients, decreased in all patients, from an average pretreatment value of 46±5.5 mm Hg to 26±3.7 mm Hg one week after botulinum toxin (FIG. 7). This represented a highly significant reduction of approximately 50 % ($p<0.007$).

Change in Esophageal Diameter

Figure 8:
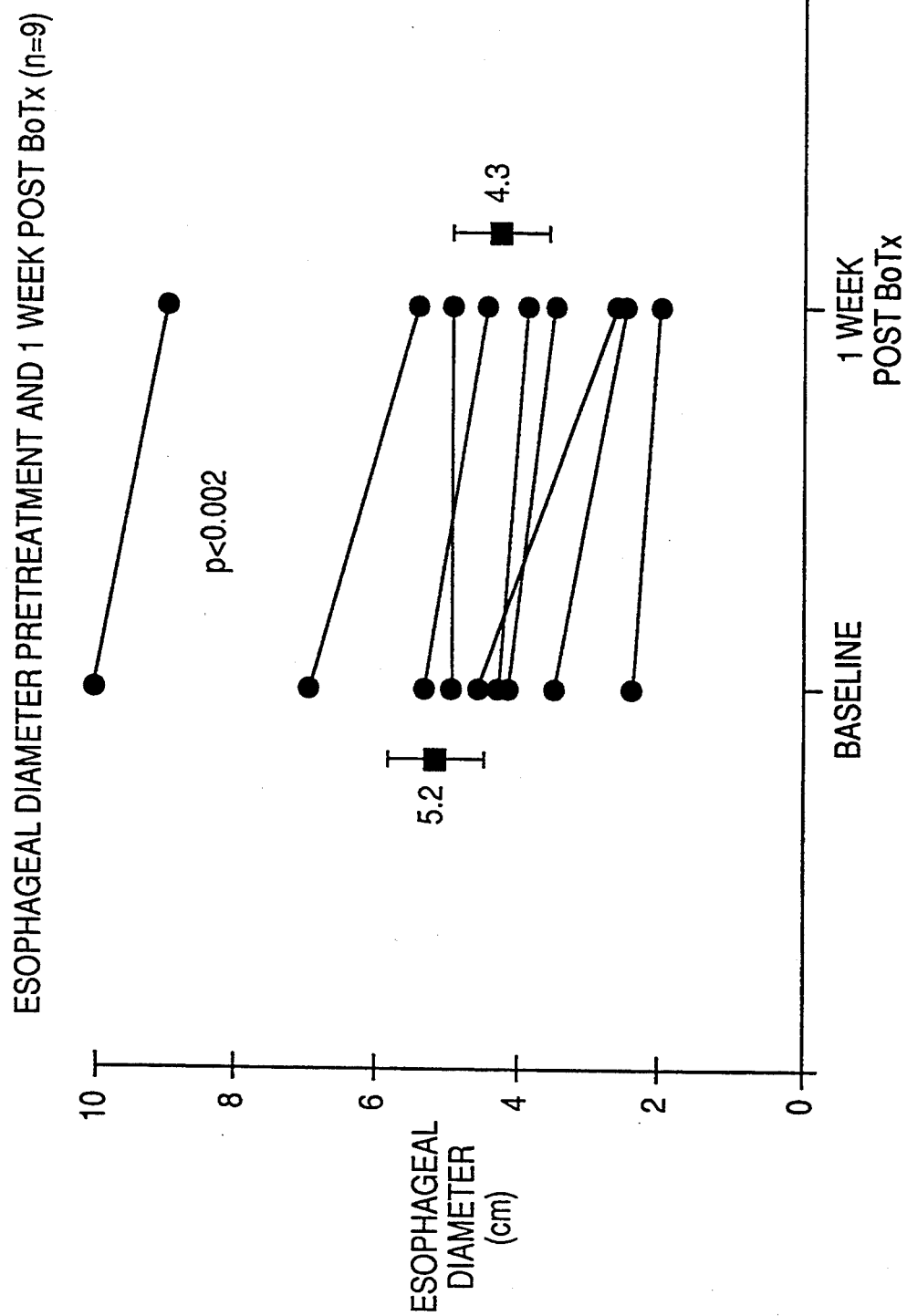
FIG. 8 shows change in maximal esophageal diameters in response to intrasphincteric botulinum toxin (BoTx) in nine patients. The numbers on the graph represent means±S.E..

Maximal esophageal diameters, available in 9 patients (FIG. 8), also decreased significantly within a week of treatment, from a pretreatment average of 5.2±0.7 to 4.3±0.7 cm, a reduction of about 20% ($p=0.002$).

Change in Esophageal Retention

Figure 9:
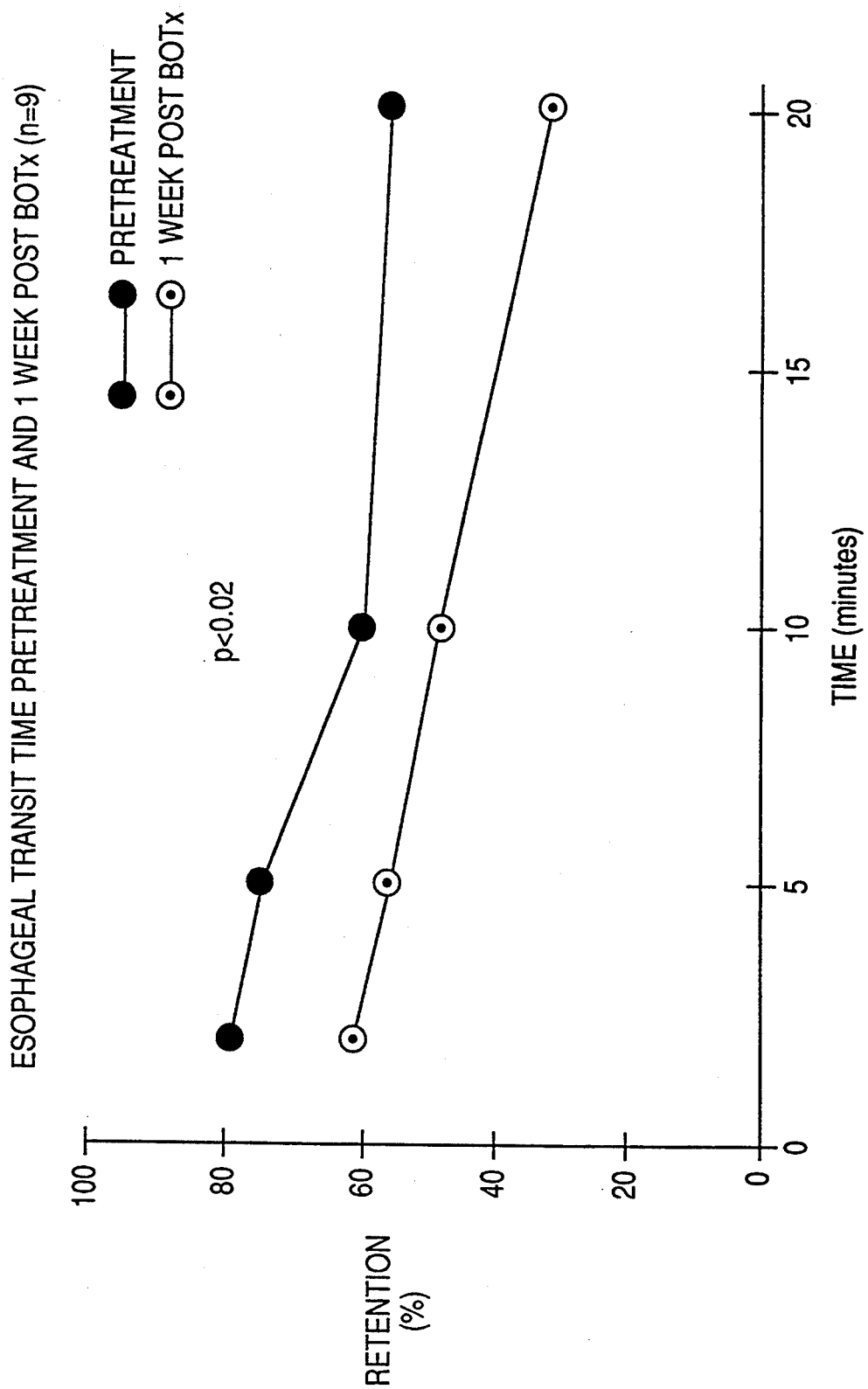
FIG. 9 shows change in esophageal retention curves, studied by a technetium labelled cornflake meal, before and after treatment with intrasphincteric botulinum toxin (BoTx) in nine patients. A significant overall difference ($p<0.02$) is seen between the two curves, with 5-minute retention decreasing to an average of 56±13% compared to a pretreatment mean of 75±8.9% ($p<0.02$), and 20-minute retention decreasing to 42±14% from a pretreatment average of 57±11.2% ($p<0.05$).

FIG. 9 shows the effects of treatment on esophageal retention, available in nine patients. A significant overall difference ($p<0.02$) is seen between the two curves, with 5-minute retention decreasing from a pretreatment mean of 75±8.9% to an average of 56±13% after treatment ($p<0.02$), and 20-minute retention decreasing from a pretreatment average of 57±11.2 % to 42±14% ($p<0.05$).

Long-Term Follow-Up

Figure 10:
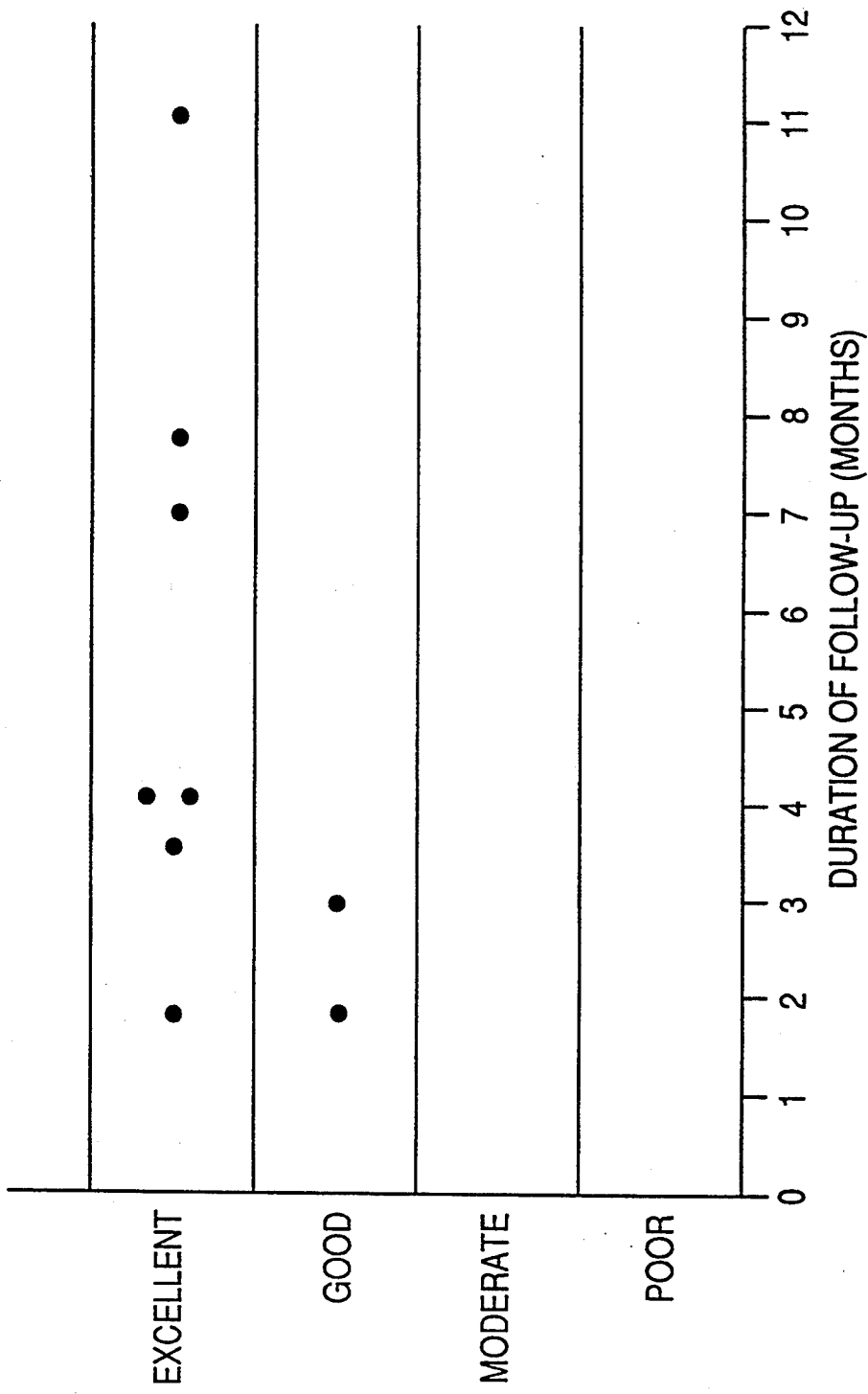
FIG. 10 shows long-term follow up of nine responders using the Vantrappen criteria. Seven patients (represented by dots in the excellent range) have remained asymptomatic at the time of writing this report while the response in the other two remains good.

We have followed these patients now for a median of 4 months (range 1–11 months). As can be seen from FIG. 10, seven of the 9 initial responders have remained asymptomatic, while the response in the other two is classifiable as good. Seven patients have received only one injection, including the three with the longest follow-up. Of five patients who had lost weight before enrollment in this study, four have reported gaining an average of 17 lb. since treatment with botulinum toxin. Our first patient has remained asymptomatic for nearly a year after a single injection and has gained 40 lb. of weight.

Complications

No adverse effects were seen in these patients during the course of this study.

Example 3

This example demonstrates the successful use of direct injection of botulinum toxin into the sphincter of Oddi (SO).

SO dysfunction has been implicated in an increasing number of gastrointestinal disorders such as postcholecystectomy syndrome and idiopathic pancreatitis. The treatment of choice for SO dysfunction is endoscopic sphincterotomy (ES) which has associated risks of pancreatitis and perforation.

A 43-year-old woman who had a cholecystectomy 8 years previously presented with biliary type pain. Her past history was significant for cirrhosis of the liver with associated portal hypertension and coagulopathy. ERCP with SO manometry (performed using standard station pull-through techniques) revealed a dilated biliary tree without other abnormalities and elevated SO pressures to 57mm/Hg. In view of her coagulopathy the patient was felt to be at an increased risk of complications from ES and was treated using local injection of BoTx into the SO.

Twenty units (2 cc) of BoTx was injected with a 5 mm sclerotherapy needle in 0.5 cc increments in a longitudinal axis from the superior border of the bile duct orifice to the horizontal fold of the papilla. Within 24 hours the patient's biliary type pain had resolved completely. Follow-up ERCP with SO manometry was performed 1 week later. The manometric results were read by an interpreter blinded to the intervention and the baseline pressure measured to be 26 mm/Hg, a reduction of 50% of pretreatment levels. The patient has remained asymptomatic to present with a follow-up of 4 weeks.

We claim:

1. A method for in vivo treatment of smooth muscle disorders of a mammal, comprising:
   injecting directly into a smooth muscle in a mammal an amount of a neurotoxin which inhibits neurotransmitter release from nerve terminals.

2. The method for claim 1 wherein said amount of neurotoxin is sufficient to reduce spasm or tone of said smooth muscle.

3. The method of claim 1 wherein said neurotoxin inhibits acetylcholine release from nerve terminals.

4. The method of claim 1 wherein the muscle is in the mammal's gastrointestinal tract.

5. The method of claim 1 wherein the muscle is in the mammal's uterus.

6. The method of claim 1 wherein the muscle is in the mammal's blood vessels.

7. A method for in vivo treatment of disorders of a gastrointestinal muscle in the enteric nervous system of a mammal, comprising:
   injecting directly into a tissue of enteric nervous system in a mammal an amount of a neurotoxin which inhibits neurotransmitter release from nerve terminals.

8. The method of claim 7 wherein said amount of said neurotoxin is sufficient to reduce spasm or tone of said gastrointestinal muscle in the enteric nervous system.

9. The method of claim 7 wherein said amount of said neurotoxin is sufficient to alleviate symptoms of said disorders of a gastrointestinal muscle in the enteric nervous system of a mammal.

10. The method of claim 7 wherein said neurotransmitter is acetylcholine.

11. The method of claim 7 wherein said gastrointestinal muscle in the enteric nervous system is a smooth muscle.

12. The method of claim 7 wherein said gastrointestinal muscle in the enteric nervous system is a skeletal muscle.

13. The method of claim 12 wherein the muscle is the cricopharyngeus.

14. The method of claim 11 wherein the muscle is the pylorus.

15. The method of claim 11 wherein the muscle is the lower esophageal sphincter.

16. The method of claim 11 wherein the muscle is the sphincter of Oddi.

17. The method of claim 11 wherein the muscle is the internal anal sphincter.

18. The method of claim 1 or 7 wherein the neurotoxin is injected via a needle which is passed through an endoscope.

19. The method of claim 1 or 7 wherein the neurotoxin is selected from the group consisting of botulinum toxin, tetanus toxin, and tetrodotoxin.

20. The method of claim 1 or 7 wherein the neurotoxin is botulinum toxin.

21. The method of claim 1 or 7 wherein the neurotoxin is botulinum toxin type A.

22. The method of claim 1 or 7 wherein the effective amount consists of between about 0.1 and 1000 units of neurotoxin.

23. The method of claim 1 or 7 wherein the effective amount consists of between about 0.1 and 100 units of neurotoxin.

24. The method of claim 1 or 7 wherein the effective amount consists of between about 10 and 100 units of neurotoxin.

* * * * *

UNITED STATES PATENT AND TRADEMARK OFFICE
CERTIFICATE OF CORRECTION

PATENT NO. : 5,437,291
DATED : August 1, 1995
INVENTOR(S) : Pankai J. Pasricha and Anthony N. Kalloo It is certified that error appears in the above-identified patent and that said Letters Patent is hereby corrected as shown below:

On the title page, insert Item [73],

<u>Assignee</u>

The Johns Hopkins University, Baltimore, Md.

Signed and Sealed this

Thirtieth Day of December, 1997

*Attest:*

BRUCE LEHMAN

*Attesting Officer*    *Commissioner of Patents and Trademarks*